(12) United States Patent
Kumar et al.

(10) Patent No.: US 7,399,860 B2
(45) Date of Patent: Jul. 15, 2008

(54) MANUFACTURE OF POLYGLUTAMATE-THERAPEUTIC AGENT CONJUGATES

(75) Inventors: Anil M. Kumar, Puyallup, WA (US); J. Peter Klein, Vashon, WA (US); Rama Bhatt, Shoreline, WA (US); Edward Vawter, Lynnwood, WA (US)

(73) Assignee: Cell Therapeutics Inc., Seattle, WA (US)

( * ) Notice: Subject to any disclaimer, the term of this patent is extended or adjusted under 35 U.S.C. 154(b) by 215 days.

(21) Appl. No.: 10/404,152

(22) Filed: Apr. 2, 2003

(65) Prior Publication Data

US 2003/0224971 A1    Dec. 4, 2003

Related U.S. Application Data

(63) Continuation of application No. 09/686,627, filed on Oct. 12, 2000, now abandoned.

(60) Provisional application No. 60/159,135, filed on Oct. 12, 1999.

(51) Int. Cl.
*C07D 471/00* (2006.01)

(52) U.S. Cl. .................. 546/48; 514/279; 514/283; 530/345; 562/575

(58) Field of Classification Search ............... 546/48, 546/41; 514/279, 283, 2; 530/345; 562/575
See application file for complete search history.

(56) References Cited

U.S. PATENT DOCUMENTS

| 4,356,166 | A | | 10/1982 | Peterson et al. |
|---|---|---|---|---|
| 5,629,433 | A | | 5/1997 | Zheng et al. |
| 5,892,043 | A | * | 4/1999 | Tsujihara et al. ............. 546/48 |
| 5,977,163 | A | | 11/1999 | Li et al. |
| 6,441,025 | B2 | * | 8/2002 | Li et al. ...................... 514/449 |
| 6,617,456 | B1 | * | 9/2003 | Tsujihara et al. ............. 546/48 |

FOREIGN PATENT DOCUMENTS

| WO | WO 97/33552 A1 | 9/1997 |
|---|---|---|
| WO | WO 99/49901 A1 | 10/1999 |
| WO | WO 01/70275 A2 | 9/2001 |

OTHER PUBLICATIONS

Doonan, "Ch. 13 Bulk Purification by Fractional Precipitation," Methods in Molecular Biology, 1996, pp. 135-144, vol. 59: Purification Protocols, Humana Press Inc., Totowa, New Jersey.

Richardson et al., "A New Biochemical Engineering Approach to the Fractional Precipitation of Proteins," Biotechnology and Bioengineering, 1990, pp. 354-366, vol. 36, No. 4, John Wiley & Sons Inc.

Scopes, "Ch. 3, Separation by Precipitation," *Protein Purification, Principles and Practice*, 1982, pp. 39-66, Springer-Verlag, New York.

Scopes, "Ch. 5 Salting Out: Ammonium Sulfate Precipitation," *Proteins Labfax*, 1996, pp. 31-32, Academic, San Diego, CA.

Zimmerman et al., "The Precipitation of Poly-$_L$-Glutamic Acid. I. α-Precipitation," *Biopolymers*, 1975, pp. 567-584, vol. 14, John Wiley & Sons Inc.

Zimmerman et al., "The Precipitation of Poly-$_L$-Glutamic Acid. II. α-Precipitation," *Biopolymers*, 1975, pp. 585-596, vol. 14, John Wiley & Sons Inc.

Yoshinori Kato et al., "A Novel Method of Conjugation of Daunomycin with Antibody with a Poly-L-glutamic Acid Derivative as Intermediate Drug Carrier. An Anti-α-fetoprotein Antibody-Daunomycin Conjugate", J. Med. Chem. 1984, 27, 1602-1607.

Conover et al., "Camptothecin Delivery Systems: Enhanced Efficacy and Tumor Accumulation of Camptothecin Following its Conjugation to Polyethylene Glycol via a Glycine Linker," *Cancer Chemother. Pharmacol.*, 1998, pp. 407-414, vol. 42, © Springer-Verlag.

de Vries et al., "Conjugation of Docetaxel (DTXL) to Poly L-Glutamic Acid (PG) Increases Anti-Tumor Efficacy," *Proceedings of the American Association for Cancer Research*, Mar. 2000, p. 323, vol. 41.

Conover et al., "Camptothecin Delivery Systems: The Utility of Amino Acid Spacers for the Conjugation of Camptothecin with Polyethylene Glycol to Create Prodrugs," *Anti-Cancer Drug Design*, 1999, pp. 499-506, vol. 14, © Oxford University Press.

Duncan et al., "Polymer-Drug Conjugates, PDEPT and PELT:Basic Principles for Design and Transfer from the Laboratory to Clinic," *Journal of Controlled Release*, 2001, pp. 135-146, vol. 74, © 2001 Elsevier Science B.V.

Greenwald, "Camptothecin-20-PEG Ester Transport Forms:the Effect of Spacer Groups on Antitumor Activity", *Bioorganic & Medicinal Chemistry*, 1998, pp. 551-562, vol. 6, © 1998 Elsevier Science Ltd.

Li et al., "Complete Regression of Well-Established Tumors Using a Novel Water-Soluble Poly-(L-Glutamic Acid)-Paclitaxel Conjugate," *Cancer Research*, Jun. 1, 1998, pp. 2404-2409, vol. 58.

Mathew, "Synthesis and Evaluation of Some Water-Soluable Prodrugs and Derivatives of Taxol with Antitumor Activity", *J. Med. Chem*, 1992, pp. 145-151, vol. 35, © American Chemical Society.

Singer et al., "Conjugation of Camptothecins to Poly-(L-Glutamic Acid)," *Annals of New York Academy of Sciences*, 2000, pp. 136-150.

Zheng et al., "Deacetylation of Paclitaxel and Other Taxanes", *Tetrahedron Letters*, 1995, pp. 2001-2004, vol. 36, No. 12, © Elsevier Science Ltd.

* cited by examiner

*Primary Examiner*—David Lukton
(74) *Attorney, Agent, or Firm*—Foley & Lardner LLP (57) ABSTRACT

The invention provides new processes for preparing polyglutamic acid-therapeutic agent conjugates for clinical development and pharmaceutical use, and polyglutamic acid-therapeutic agent conjugates prepared by these processes.

25 Claims, 7 Drawing Sheets

FIGURE 1 poly-l-glutamic acid-glycyl-20(S)camptothecin poly-L-glutamic acid-2'-(glycyl) paclitaxel poly-L-glutamic acid-2'-docetaxel

FIGURE 2

Manufacturing Scheme

Poly-L-glutamic acid sodium salt

1. Dissolve in water
2. Acidify to pH 2 with 1M HCl
3. Separate the solid by centrifugation
4. Wash with water until pH >3.5
5. Lyophilize Poly-L-glutamic acid 1. Paclitaxel, dimethylaminopyridine, diisopropylcarbodiimide, dimethylformamide, stir until reaction is complete
2. Dilute with 10% NaCl solution (Volume 2.5 times of DMF)
3. Filter
4. Wash several times with water
5. Lyophilize
6. Slurry with MeCN
7. Vacuum Dry CT 2103           Yield = average 87% for 10 lots

Reaction Scheme I

Reaction Scheme II

MANUFACTURE OF POLYGLUTAMATE-THERAPEUTIC AGENT CONJUGATES

This application is a continuation of application 09/686627, filed Oct. 12, 2000, now abandoned, which claims priority to provisional application 60/159135, filed Oct. 12, 1999.

FIELD OF THE INVENTION

This invention relates to a process for scaled-up manufacture of polyglutamate-therapeutic agent conjugates for clinical development.

BACKGROUND OF THE INVENTION

The antitumor agent paclitaxel shows increased efficacy and decreased toxicity when administered to tumor-bearing hosts as a polyglutamic acid conjugate compared with the unconjugated form of the drug (U.S. Pat. No. 5,977,163; Li et al., Cancer Res., 58:2404, 1998). The polyglutamic acid-paclitaxel conjugate shows increased water solubility, a slower clearance from the body, and an increased accumulation in the tumor. Conjugates of polyglutamic acid and various other therapeutic agents are expected to provide clinically useful alternatives to the presently available formulations.

For research purposes, the polyglutamic acid-therapeutic agent conjugates can be produced by the method disclosed in Li et al., ibid. In that method, the conjugate is prepared as a sodium salt, dialyzed to remove low molecular weight contaminants and excess salt and then lyophilized. The method is not well-suited for large-scale manufacture of quantities of conjugates for clinical development and use, however. In particular, the use of dialysis to remove impurities is time-consuming and lowers final product yield. In addition, although many pharmaceuticals have more favorable properties when prepared as salts (e.g., improved solubility, storage, and handling), this is not true of the polyglutamate-therapeutic agent conjugates of the present invention. The salt forms of the conjugates are electrostatic solids, not free flowing powders. They are more difficult to package, more susceptible to dust contamination and more likely to contaminate the workplace with cytotoxic agents than are free flowing powders. Therefore, there is a need for an improved process of manufacture of polyglutamic acid-therapeutic agent conjugates that can be used to produce gram to hundreds of gram quantities of these conjugates in high yields and in a manner that provides for improved materials handling and packaging.

SUMMARY OF THE INVENTION

The present invention satisfies this need by providing an improved process for preparing a polyglutamic acid-therapeutic agent conjugate that is capable of providing gram to kilogram quantities of pharmaceutical grade conjugate with yields of between 85% and 98% or between about 85% to about 98%.

In one embodiment, the process comprises:
(a) providing the protonated form of a polyglutamic acid polymer and a therapeutic agent for conjugation thereto;
(b) covalently linking said agent to said polyglutamic acid polymer in an inert organic solvent to form a polyglutamic acid-therapeutic agent conjugate;
(c) precipitating said polyglutamic acid-therapeutic agent conjugate from solution by addition of an excess volume of aqueous salt solution; and
(d) collecting said conjugate as a protonated solid.

Additional removal of residual low molecular weight contaminants can be carried out between step (c) and step (d) or after step (d).

In another embodiment, which is presently most preferred, in situ generation of a protonated polyglutamic acid-therapeutic agent conjugate is carried out by a process comprising:
(a) suspending a salt of a polyglutamic acid polymer in an inert organic solvent;
(b) protonating said polymer by the addition of an anhydrous acid to said suspension to form a soluble salt of the conjugate base;
(c) providing a therapeutic agent and covalently linking said agent to said polyglutamic acid polymer to form a polyglutamic acid-therapeutic agent conjugate;
(d) precipitating said polyglutamic acid-therapeutic agent conjugate from solution by the addition of an excess volume of aqueous salt solution; and
(e) collecting said conjugate as a protonated solid.

In another embodiment, the process for the large-scale manufacture of polyglutamic acid-2'paclitaxel conjugate comprises:
(a) providing an aqueous solution of the sodium salt of poly-L-glutamic acid;
(b) acidifying the solution to a pH of about 2 to 4, thereby converting the sodium salt of poly-L-glutamic acid to the protonated form and precipitating it from solution;
(c) collecting the poly-L-glutamic acid precipitate and washing with water;
(d) drying the poly-L-glutamic acid to a water content of between about 2% to about 7%, preferably between 7% and 21% and most preferably between about 7% to about 21% by weight;
(e) contacting the poly-L-glutamic acid with paclitaxel under standard coupling conditions for sufficient time to conjugate paclitaxel to the polyglutamic acid polymer via an ester linkage formed between the 2'-OH group of paclitaxel and a carboxy group of poly-L-glutamic acid;
(f) cooling the reaction mixture from between 0° C. to 10° C. or between about 0° C. to 10° C. while slowly adding aqueous salt solution to the reaction mixture;
(h) acidifying the resulting suspension;
(i) collecting the conjugate as a protonated solid; and
(j) extracting impurities from the protonated solid.

It is most preferred for the large-scale manufacture of polyglutamic acid-2'paclitaxel conjugate to substitute for steps (a)-(d) above, steps (a') and (b'):
(a') providing a suspension of poly-L-glutamic acid sodium salt, or a poly-L-glutamic acid salt of lithium, potassium, or quatnernary ammonium, in an inert organic solvent;
(b') adding about 0.95 equivalent of trifluoroacetic acid or methanesulfonic acid thereby forming a solution comprising sodium, lithium, potassium or quaternary ammonium salts of poly-L-glutamic acid trifluoroacetate or polyglutamic acid methanesulfonate; and carrying out steps (e)-(j) as described above.

Any polyglutamic acid-therapeutic agent conjugate can be prepared by the processes described herein. In one preferred embodiment, the therapeutic agents are antitumor agents, e.g., paclitaxel; docetaxel; etoposide; teniposide;

epothilones, such as epothilone A, epothilone B, epothilone C, epothilone, epothilone F and 12,13-disoxyepothilone F; gemcitabine; 20(S)(+) camptothecin; 9-aminocamptothecin; 9-nitrocamptothecin; 7-ethyl-10-hydroxycamptothecin; 9-dimethylaminomethyl-10-hydroxycamptothecin; 10,11-methylenedioxycamptothecin; 7-methylpiperizinomethyl-10,11-ethylenedioxycamptothecin; flavopiridol; geldanamycin; 17-(allylamino)-17-demethoxygeldanamycin; ecteinascidin 743; phthalascidin; CT-2584 (1-(11-(dodecylamino)-10-hydroxyundecyl)-3,7-dimethylxanthine; CT-4582 (1-(11-(N-methyl N-dodecyl amino)-10-hydroxyundecyl)-3,7-dimethylxanthine); doxorubicin; adriamycinone; melphalan; fludarabine; daunomycin; verapamil; 5-fluorouracil; floxuridine (FUDR); cyclosporin; retinoic acids; 7-dimethyl-tert-butylsilyloxy)-10-hydroxy camptothecin and others.

DETAILED DESCRIPTION OF THE INVENTION

Definitions

As used herein, "a polyglutamic acid" or "polyglutamic acid polymer" includes poly (1-glutamic acid), poly (d-glutamic acid) and poly (dl-glutamic acid). Preferably the polyglutamic acid polymer comprises at least 50% of its amino acid residues as glutamic acid, and more preferably, 100%. The polyglutamic acid polymer can be substituted up to 50% by naturally occurring or chemically modified amino acids, preferably hydrophilic amino acids, provided that when conjugated to a therapeutic agent, the substituted polyglutamic acid polymer has improved aqueous solubility and/or improved efficacy relative to the unconjugated therapeutic agent, and is preferably nonimmunogenic.

The molecular weight of the polyglutamic acid polymer used in the preparation of the conjugate by the methods described herein is typically greater than 5000 daltons, preferably from 15 kd to 80 kd, more preferably 20 kd to 80 kd, even more preferably from 20 kd to 60 kd, and most preferably from 30 kd to 60 kd (as determined by viscosity). At the lower end of molecular weight, the polyglutamic acid polymers of this invention have a molecular weight of about 10,000, about 11,000, about 12,000, about 13,000, about 14,000, about 15,000, about 16,000, about 17,000, about 18,000, about 19,000, about 20,000, about 21,000, about 22,000, about 23,000, about 24,000, about 25,000, about 26,000, about 27,000, about 28,000, about 29,000, to about 30,000 daltons. At the higher end, the polyglutamic acid polymers of this invention have a molecular weight of about 31,000, about 32,000, about 33,000, about 34,000, about 35,000, about 36,000, about 37,000, about 38,000, about 39,000, about 40,000, about 41,000, about 42,000, about 43,000, about 44,000, about 45,000, about 46,000, about 47,000, about 48,000, about 49,000, about 50,000, about 51,000, about 52,000, about 53,000, about 54,000, about 55,000, about 56,000, about 57,000, about 58,000, about 59,000, about 60,000, about 61,000, about 62,000, about 63,000, about 64,000, about 65,000, about 66,000, about 67,000, about 68,000, about 69,000, about 70,000, about 71,000, about 72,000, about 73,000, about 74,000, about 75,000, about 76,000, about 77,000, about 78,000, about 79,000, to about 80,000 daltons. Those skilled in the art will appreciate that the molecular weight values may be different when measured by other methods. These other methods include, for example, gel permeation, low angle light scattering, multiple angle laser light scattering, refractive index and combinations thereof As used herein, a "polyglutamic acid-therapeutic agent conjugate" refers to a polyglutamic acid polymer that is covalently bonded to the therapeutic agent by a direct linkage between a carboxylic acid residue of the polyglutamic acid and a functional group of the therapeutic agent, or by an indirect linkage via one or more bifunctional linkers. Preferred linkers are those that are relatively stable to hydrolysis in the circulation, are biodegradable and are nontoxic when cleaved from the conjugate. Of course, it is understood that suitable linkers will not interfere with the antitumor efficacy of the conjugates. Exemplary linkers include amino acids (e.g., glycine, alanine, leucine, isoleucine), hydroxyacids (e.g., γ-hydroxybutyric acid), diols, aminothiols, hydroxythiols, aminoalcohols, and combinations of these. A therapeutic agent can be linked to the polymer or linker by any linking method that results in a physiologically cleavable bond (i.e., a bond that is cleavable by enzymatic or nonenzymatic mechanisms that pertain to conditions in a living animal organism). Examples of preferred linkages include ester, amide, carbamate, carbonate, acyloxyalkylether, acyloxyalkylthioether, acyloxyalkylester, acyloxyalkylamide, acyloxyalkoxycarbonyl, acyloxyalkylamine, acyloxyalkylamide, acyloxyalkylcarbamate, acyloxyalkylsulfonamide, ketal, acetal, disulfide, thioester, N-acylamide, alkoxycarbonyloxyalkyl, urea, and N-sulfonylimidate.

Methods for forming these linkages are well known to those skilled in synthetic organic chemistry, and can be found, for example, in standard texts, such as J. March, Advanced Organic Chemistry, Wiley Interscience, 4$^{th}$ Edition.

The degree of loading of bioactive, therapeutic or diagnostic agent on the polymer (i.e., the "loading density") may be expressed as the number of molecules or average number of molecules per polyglutamic acid polymer chain or preferably as a percent (%) of total weight of the conjugate ("% loading"). A desired % loading can be obtained by adjusting the ratios of the therapeutic agent and polymer, and optimizing other reagents as necessary. The optimal loading density for a given conjugate and given use is determined empirically based on the desired properties of the conjugate (e.g., water solubility, therapeutic efficacy, pharmacokinetic properties, toxicity and dosage requirements). The loading density ranges from between 1% to about 60% or from about 1% to about 60%, preferably from 5% to 55% or from about 5% to about 55%, and more preferably from 10% to 45% or from about 10% to about 45% for the conjugates that are specifically described herein.

The % loading is typically determined by four methods: (1) calculated weight % (2) spectrophotometry, preferably UV spectrophotometry; (3) NMR ratio method; and (4) hydrolysis method.

(1) The calculated weight % is based on the known weight of the polyglutamic acid starting material and the weight of the therapeutic agent. For all conjugates, the conversion to conjugate form is 100% complete, as determined by TLC on silica.

(2) The spectrophotometry method, preferably UV spectrophotometry, is based on the weight % of the therapeutic agent as measured by absorbance at an appropriate wavelength (e.g., UV absorbance), or fluorescence, as exemplified for a paclitaxel-polyglutamic acid conjugate. The conjugate is dissolved in deionized water (2.5 or 5 mg/mL), centrifuged at 500 g for 15 minutes to remove particulate matter if present, and the clear solution is diluted 100× to 200× with deionized water. The absorbance is read against the diluent at a specified wavelength, e.g. UV absorption is read against the diluent at 228 nm or 260 nm. A solution of the same lot of polyglutamic acid used to prepare the conjugate is dissolved at the same nominal concentration as the conjugate and its absorbance is read against the diluent, e.g., at 228 nm or 260 nm. A linear calibration curve is prepared by measuring the absorbance, e.g., at 228 nm or 260 nm, of solutions of known concentrations of the paclitaxel dissolved in methanol. To calculate the percent loading, the absorbance of the polyglutamic acid solution (corrected to account for the theoretical loading of polyglutamic acid in the polyglutamic acid-paclitaxel solution) is subtracted from the polyglutamic acid-paclitaxel absorbance. This corrected absorbance is compared to the paclitaxel standard curve to obtain the paclitaxel concentration (w/v) in the conjugate solution. The percent loading is the ratio of the paclitaxel concentration to the polyglutamic acid-paclitaxel conjugate concentration times 100.

(3) The NMR ratio method is based on the weight % of therapeutic agent as measured by the ratio of the peaks in the spectra resulting from the polymer in relation to the peaks from the therapeutic agent. This is illustrated below for polyglutamic acid-paclitaxel conjugate.

The area between about 4.5 ppm to about 6.5 ppm, preferably 4.5 ppm and 6.5 ppm, is totalled and divided by the number of protons (7). This number is then compared to the area between about 3.8 ppm to about 4.4 ppm, preferably 3.8 ppm to 4.4 ppm, for the polymer backbone and is corrected for 2 protons from paclitaxel that overlap. The two areas per proton are compared taking into account the molecular weights of the paclitaxel and the polymer.

A=area per proton for polymer÷area per proton for paclitaxel=21.36/1.98=10.79.

MW paclitaxel=837; MW of polyglutamic acid monomer is 129.

% loading=(837/(10.79×129)+837)×100=37.6%.

The processes described herein are generally useful for preparing conjugates of polyglutamic acid with any bioactive, therapeutic or diagnostic agent that is appropriately functionalized for linking to the polyglutamic acid, as described herein. The conjugates that are exemplified herein are intended to illustrate the invention, but not to limit its scope.

In one preferred embodiment, the therapeutic agents comprise drugs that are effective in treating cancerous conditions that are expected to benefit from the unique pharmacokinetic properties of these conjugate (e.g., enhanced permeability and retention in tumor tissue, sustained release of active agent, long biological half life compared with the unconjugated agent, and others). Presently preferred agents include, by way of example, taxanes (e.g., paclitaxel, docetaxel); etoposide; teniposide; epothilones, such as epothilone A, epothilone B, epothilone C, epothilone D, epothilone F and 12,13-disoxyepothilone F; gemcitabine; 20(S)(+) camptothecin; 9-aminocamptothecin; 9-nitrocamptothecin; 7-ethyl-10-hydroxycamptothecin; 9-dimethylaminomethyl-10-hydroxycamptothecin; 10,11-methylenedioxycamptothecin; 7-methylpiperizinomethyl-10,11-ethylenedioxycamptothecin; flavopiridol; geldanamycin; 17-(allylamino)-17-demethoxygeldanamycin; ecteinascidin 743; phthalascidin; CT-2584 (1-(11-(dodecylamino)-10-hydroxyundecyl)-3,7-dimethylxanthine; CT-4582 (1-(11-(N-methyl N-dodecyl amino)-10-hydroxyundecyl)-3,7-dimethylxanthine); doxorubicin; adriamycinone; melphalan; fludarabine; daunomycin; verapamil; 5-fluorouracil; floxuridine (FUDR); cyclosporin; retinoic acids; 7-dimethyl-tert-butylsilyloxy)-10-hydroxy camptothecin and others.

The therapeutic agent must be capable of attachment to the polymer by means of a functional group that is already present in the native molecule or otherwise can be introduced by well-known procedures in synthetic organic chemistry without altering the activity of the agent. In the examples given herein, the agent is relatively water-insoluble in the unconjugated form and shows greatly improved solubility following conjugation. However, water-soluble drugs are also expected to show advantages following their conjugation to polyglutamic acid (e.g., improved pharmacokinetics and retention at the site of action compared to the unconjugated agent).

Reactions performed under "standard coupling conditions" are carried out in an inert solvent (e.g., DMF, DMSO, N-methylpyrrolidone) at a temperature from −20° C. to 150° C. or from about −20° C. to about 150° C., preferably from 0° C. to 70° C. or from about 0° C. to about 70° C., more preferably from 5° C. to 30° C. or from about 5° C. to about 30° C., in the presence of a coupling reagent and a catalyst. Of course, the temperature used will depend on factors such as the stability of the therapeutic agent and the reactivity of the attaching group. Suitable coupling reagents are well-known in synthetic organic chemistry and include, but are not limited to, carbodiimides, alkyl chloroformate and triethylamine, pyridinium salts-tributyl amine, phenyl dichlorophosphate, 2-choro-1,3,5-trinitrobenzene and pyridine, di-2-pyridyl carbonate, polystyryl diphenylphosphine, (trimethylsilyl) ethoxyacetylene, 1,1'-carbonylbis(3-methylimidazolium)triflate, diethylazodicarboxylate and triphenyl phosphine, N,N'-carbonyldiimidazole, methanesulphonyl chloride, pivaloyl chloride, bis(2-oxo-3-oxazolidinyl)phosphinic acid ("BOP-Cl"), 2-chloromethylpyridinium iodide ("CMPI"), and the like. Suitable catalysts for alcohol coupling include organic bases, e.g., 4-N,N-dimethylaminopyridine and 4-pyrollidinopyridine.

As used herein, the term "inert solvent" means a solvent inert under the conditions of the reaction being described in conjunction therewith [including, for example, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$"), diethyl ether, ethyl acetate, acetone, methylethyl ketone, dioxane, pyridine, dimethoxyethane, t-butyl methyl ether, and the like]. Unless specified to the contrary, the solvents used in the reactions of the present invention are inert solvents.

If multiple functional groups are present on the therapeutic agent, selective attachment of a particular group of the agent to the polyglutamic acid polymer will require the use of a suitable protecting group. The term "protecting group" or "blocking group" refers to any group which when bound to one or more hydroxyl, thiol, amino or carboxyl groups of the compounds prevents reactions from occurring at these groups and which protecting group can be removed by conventional chemical or enzymatic steps to reestablish the hydroxyl, thiol, amino or carboxyl group. See, generally, T. W. Greene & P. G. M. Wuts, "Protective Groups in Organic Synthesis," 3rd Ed, 1999, John Wiley and Sons, N.Y.

The particular removable blocking group employed is not critical and preferred removable hydroxyl blocking groups include conventional substituents, such as allyl, benzyl, acetyl, chloroacetyl, thiobenzyl, benzylidine, phenacyl, t-butyl-diphenylsilyl, t-butyldimethylsilyl, triethylsilyl, MOM (methoxymethyl), NEM (2-methoxyethoxymethyl), t-BOC (tert-butyloxycarbonyl), CBZ (benzyloxycarbonyl) and any other group that can be introduced chemically onto a hydroxyl functionality and later selectively removed either by chemical or enzymatic methods in mild conditions compatible with the nature of the product.

Preferred removable amino blocking groups include conventional substituents, such as t-butyloxycarbonyl (t-BOC), benzyloxycarbonyl (CBZ), fluorenylmethoxycarbonyl (FMOC), allyloxycarbonyl (ALOC) and the like, which can be removed by conventional conditions compatible with the nature of the product.

In another embodiment, pyro-derivatized amino blocking groups, such pyroglutamic acid, can be used. In a particular embodiment, the pyroglutamic acid may or may not be removed.

Preferred carboxyl protecting groups include esters, preferably esters containing alkyl groups such as methyl, ethyl, propyl, t-butyl etc., which can be removed by mild hydrolysis conditions compatible with the nature of the product.

Nomenclature

Figure 1:
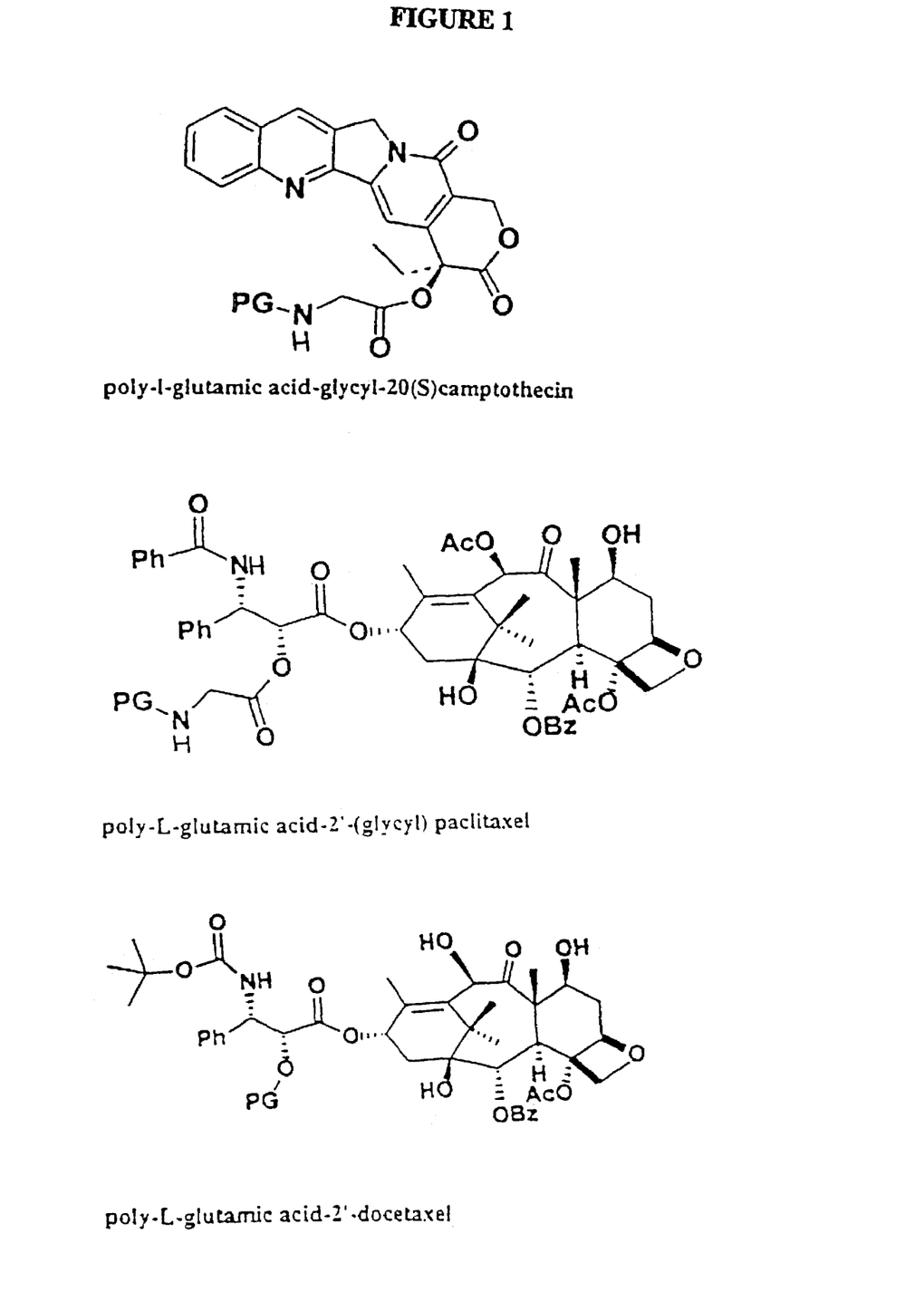
FIG. 1. Exemplary conjugates

Exemplary conjugates prepared according to the embodiments of the invention described herein are shown in FIG. 1. The conjugates in the Examples below are named in the same way as the conjugates of FIG. 1.

DESCRIPTION OF PREFERRED EMBODIMENTS

In general, the process of manufacturing polyglutamate-therapeutic agent conjugates on a scale that is suitable for clinical development and pharmaceutical use comprises the steps of:

(a) providing a protonated form of a polyglutamic acid polymer and a therapeutic agent for conjugation thereto;

(b) covalently linking said agent to said polyglutamic acid polymer in an inert organic solvent to form a polyglutamic acid-therapeutic agent conjugate;

(c) precipitating said polyglutamic acid-therapeutic agent conjugate from solution by addition of an excess volume of aqueous salt solution; and (d) collecting said conjugate as a protonated solid.

The protonated form of the polyglutamic acid polymer in step (a) is obtained by acidifying a solution containing the salt of the polyglutamic acid to be used as a starting material, and converting the salt to its acid form. After separating the solid by centrifugation, the solid is washed with water. (When dimethylaminopyridine ("DMAP") is to be used in step (b), it is preferred to wash the solid until the aqueous phase is pH 3 or greater). The polyglutamic acid is then dried, preferably by lyophilization and preferably to a constant weight comprising between about 2% to about 21% water, preferably between about 7% to about 21% water, more preferably between 7% and 21% of water, prior to conjugation to a desired therapeutic agent (step (b)).

The therapeutic agent of step (b) may require modification prior to conjugation, e.g., the introduction of a new functional group, the modification of a preexisting functional group or the attachment of a spacer molecule. Such modifications may require the use of protecting groups, which are described above.

Figure 5:
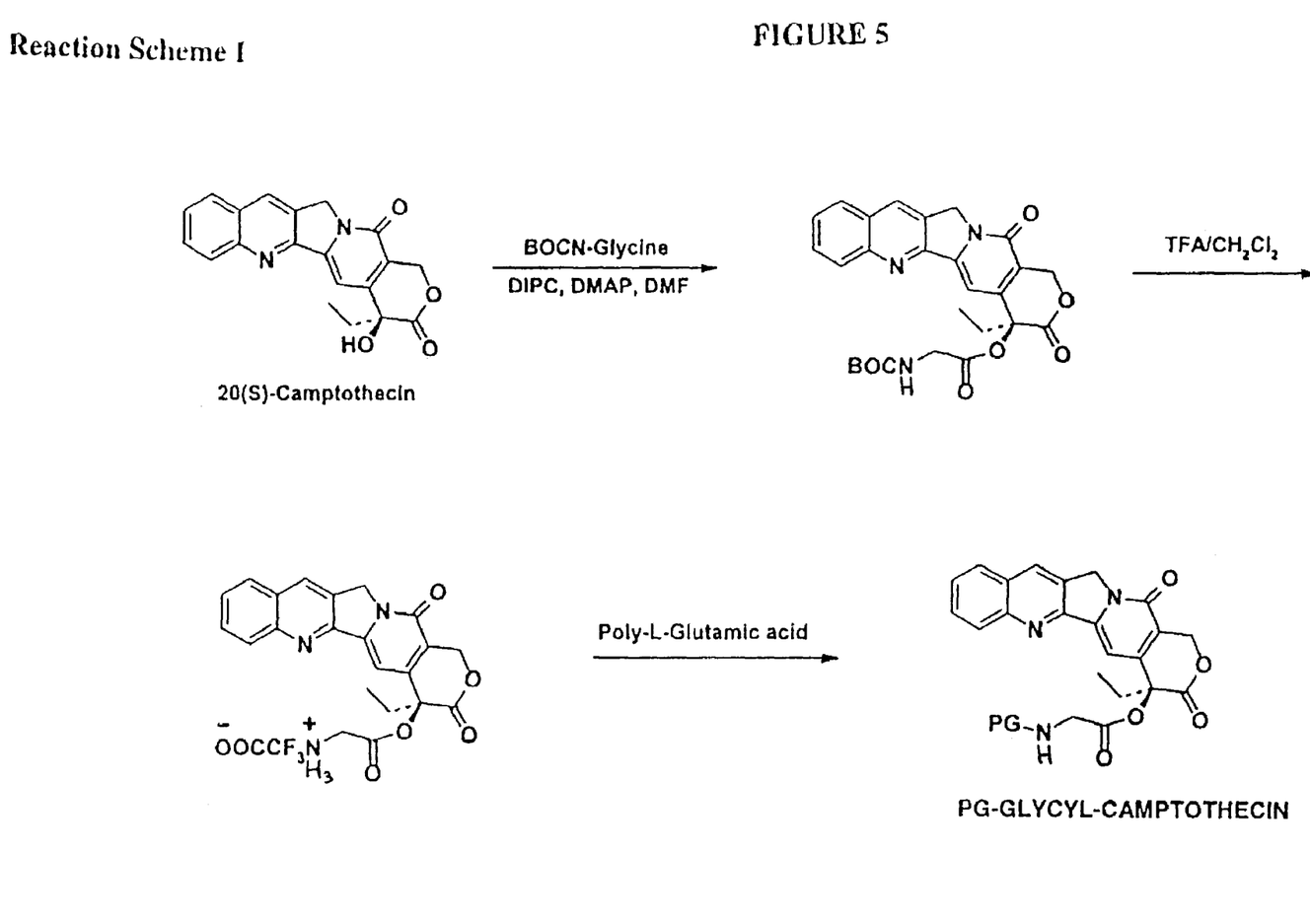
FIGS. 5-7. Reaction Schemes I-III.
Figure 6:
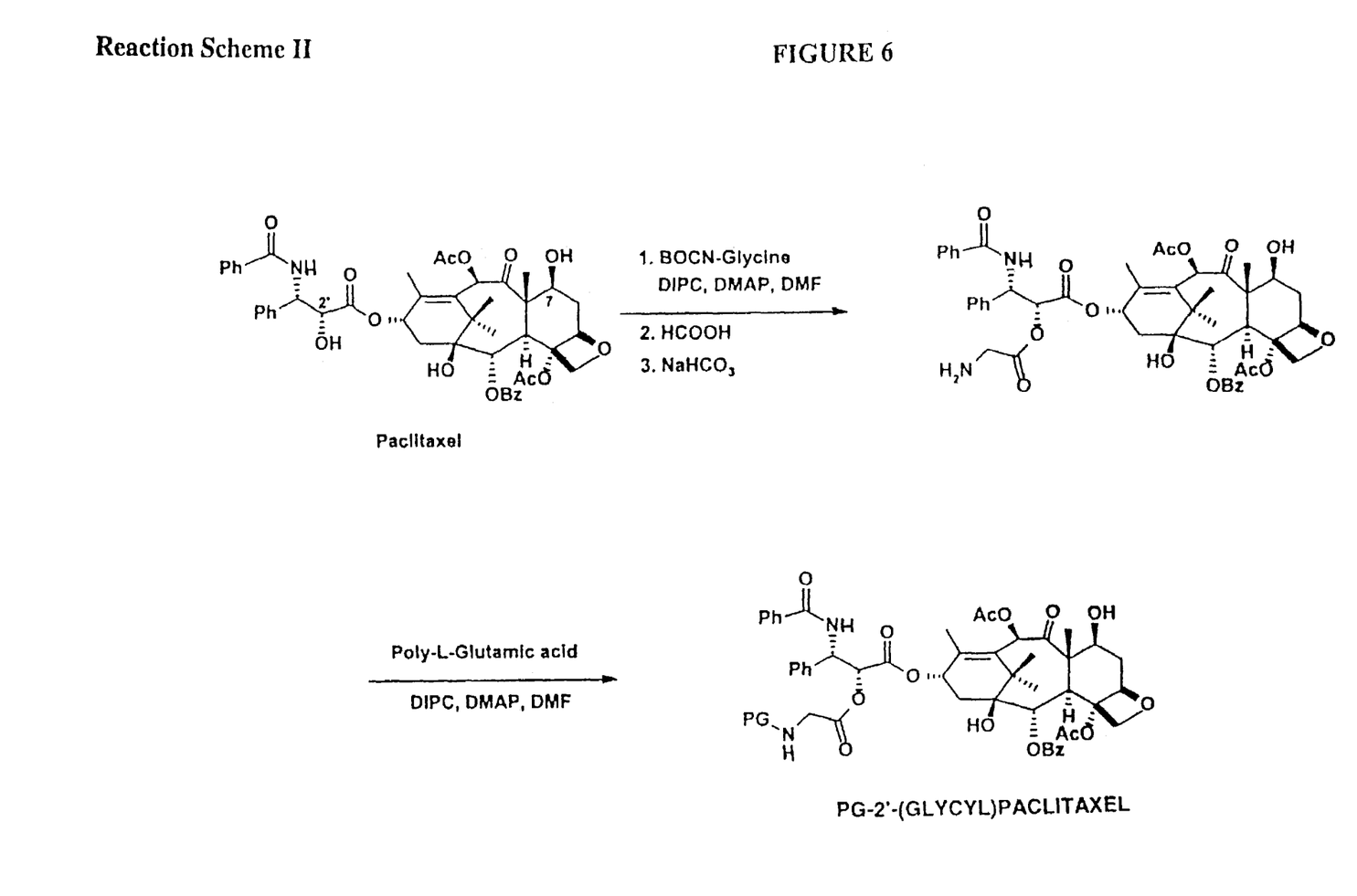
Figure 7:
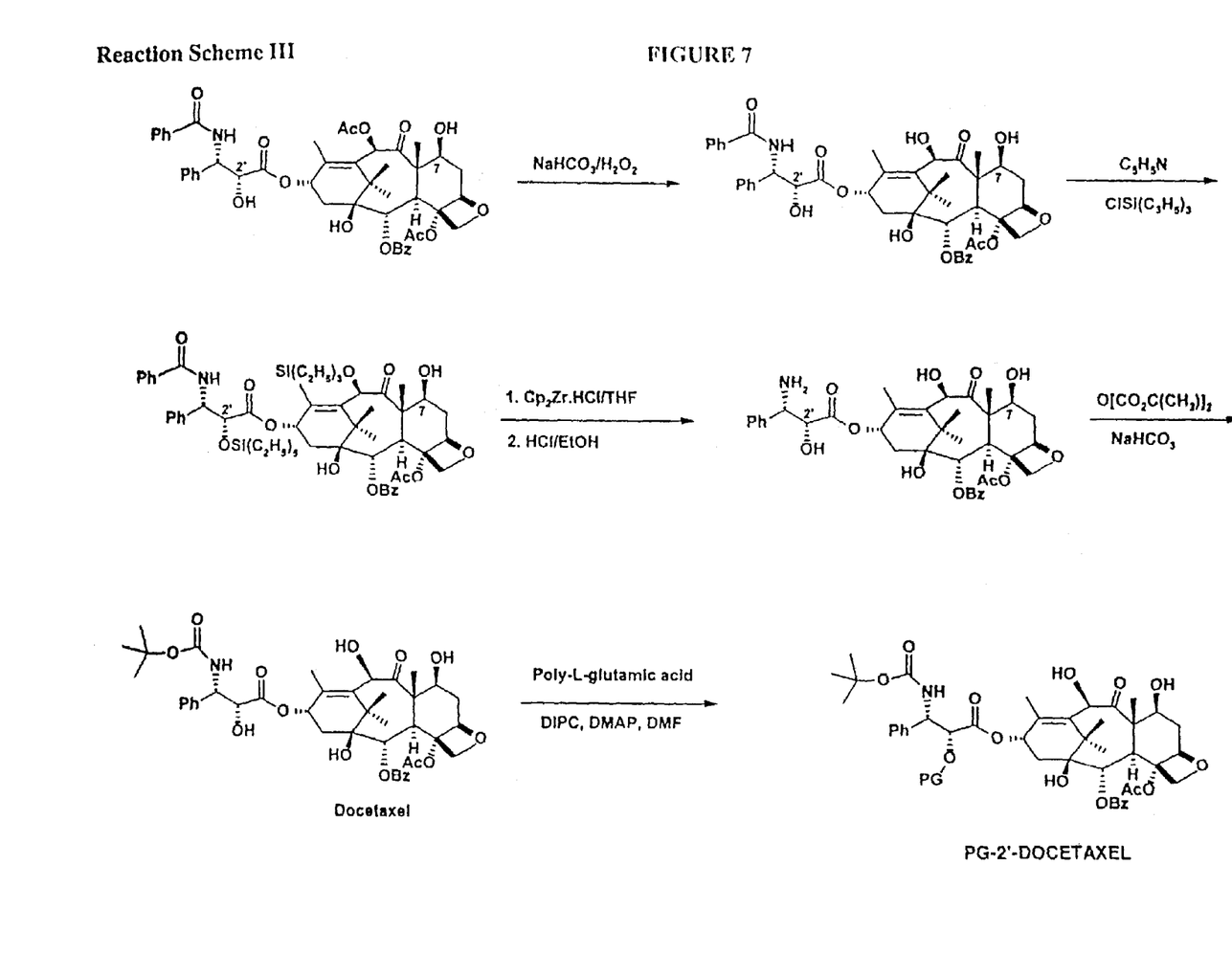

Reaction schemes I-III illustrate methods that were used for linking various exemplary therapeutic agents to poly-L-glutamic acid (PG), either directly or through glycine spacer molecules. The conditions shown in these schemes and described in the Examples may be varied, as will be readily appreciated by those skilled in synthetic organic chemistry. The exact conditions that are used for conjugating a particular therapeutic agent to polyglutamic acid may be based on the stability of the therapeutic agent to the reaction conditions, the reactivity of the linking groups, other factors pertinent to the manufacturing process (e.g., safety and regulatory issues), and the like. As described above, various types of linkages may be used in preparing the conjugates, depending on the available functional groups on the therapeutic agent and the linker molecule, if a linker is used. Thus, the therapeutic agent may be conjugated to polyglutamic acid and/or linker molecules by linkages other than ester and amide bonds. Linkers other than glycine, and coupling reagents other than those exemplified herein, can also be used. The exact conditions used for preparing the conjugates that illustrate the practice of embodiments of the present invention are described below in the Examples.

In step (c), an aqueous salt solution is added to the reaction mixture to precipitate the polyglutamic acid-therapeutic agent conjugate from solution. Any water soluble inorganic salt can be used for this purpose, such as salts of sodium, potassium and ammonium, as well as halide and sulfate salts (e.g., NaCl, KCl, $NH_4Cl$, sodium sulfate, ammonium sulfate, etc.). Preferably, 10-15% salt solution is used in 1×-4× volume. In one preferred embodiment, a 2.5× volume of 10% NaCl is used. The salt solution is added slowly to the reaction mixture, which is cooled during the addition. For optimum yield of conjugate, the temperature is kept between about 0° C. to about 10° C., preferably 0° C. and 10° C. The precipitation step separates the polyglutamic acid-therapeutic agent conjugate from starting materials and reaction byproducts that are wholly or partially soluble under the conditions used for precipitation of the conjugate.

In step (d), the conjugate is collected as the protonated solid. The suspension obtained in step (c) is preferably acidified. Depending on the stability of the drug molecule to acid conditions, a pH in the range of about pH 1 to about pH 4, preferably pH 1-4, can be used. For preparation of polyglutamic acid-paclitaxel conjugates, however, acidification below pH 2 results in the decomposition of paclitaxel, and acidification is typically carried out at about pH 2.5. Preferably, for the removal of the base, such as DMAP, and acid, such as hydrochloric acid (HCl), is used in step (d). The suspension can be filtered or centrifuged, preferably filtered, to collect the conjugate.

Figure 2:
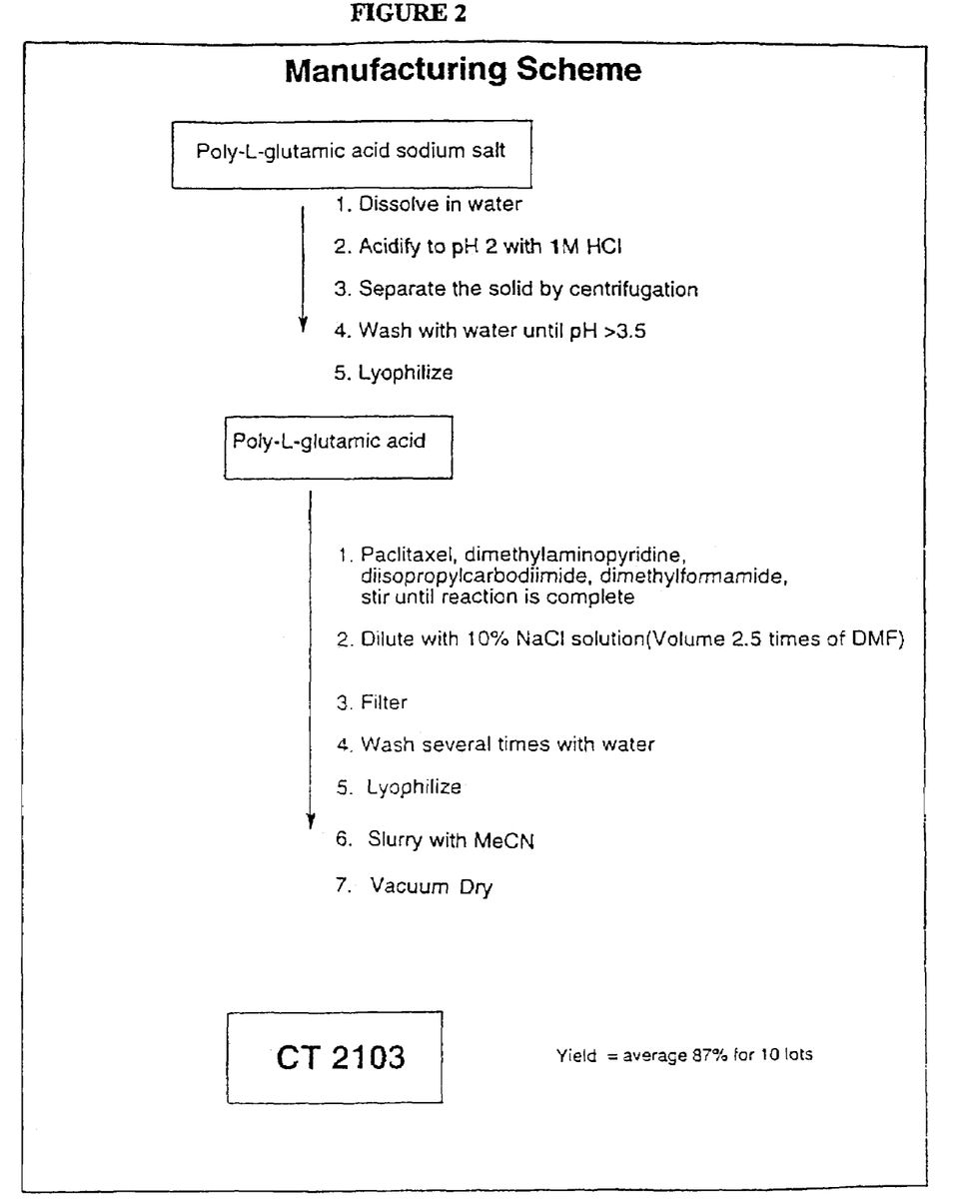
FIG. 2. Manufacturing Scheme for poly-L-glutamic acid-paclitaxel conjugate
Figure 4:
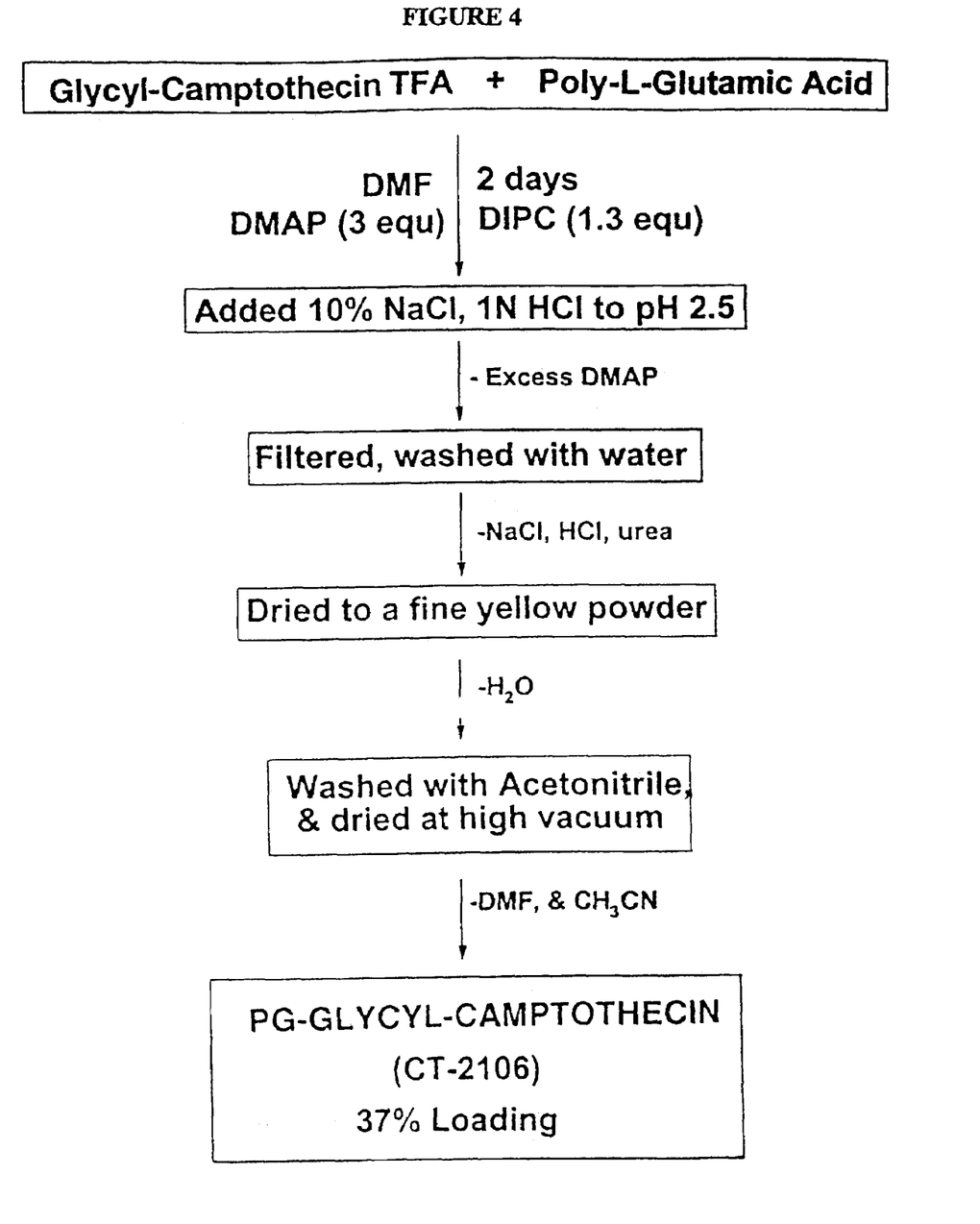
FIG. 4. Preparation of poly-L-glutamic acid-glycyl-20(S) camptothecin

Unreacted starting materials, byproducts and other impurities can be removed prior to, or after acidification to yield the final protonated conjugate (illustrated in Examples 2 and 3 below, and FIGS. 2 and 4). For example, after addition of the salt solution, the solid can be collected and resolubilized, then either filtered or extracted with an appropriate solvent in which the contaminants are soluble but the conjugate is not (e.g., ethyl acetate, methylene chloride, chloroform, hexanes, heptane, diethyl ether and dioxane). The solution is then acidified and the protonated form of the conjugate is collected as described above.

Alternatively, the solid can be lyophilized, then slurried with an appropriate solvent or mixtures thereof, e.g., acetonitrile (MeCN); ethers, such as diethyl ether, dioxane, tetrahydrofuran; halogenated solvents, such as choloform, methylene chloride; ketones, such as acetone and methylethyl ketone (MEK); $C_1$ to $C_{10}$ alcohols, such as tert-butyl alcohol, isopropyl alcohol, ethyl alcohol or methanol; to remove impurities from the final protonated conjugate product.

In an alternative preferred embodiment, step (c) above is replaced by step (c'), which comprises:

(c') separating said polyglutamic acid-therapeutic agent conjugate from unreacted starting materials and byproducts and precipitating said polyglutamic acid-therapeutic agent conjugate from solution by addition of an organic solvent in which unreacted starting materials and byproducts are soluble.

In addition to ethyl acetate and acetonitrile, examples of other solvents that can be used to purify the conjugate include chloroform, tetrahydrofuran, dioxane, toluene, 2-butylmethyl ether, and the like.

An alternative procedure is presently most preferred, wherein in situ generation of a protonated polyglutamic acid-therapeutic agent conjugate is carried out by a process comprising:

(a) suspending a salt of a polyglutamic acid polymer in an inert organic solvent, (b) protonating said polymer by the addition of an anhydrous acid to said suspension to form a soluble salt of the conjugate base;

(c) providing a therapeutic agent and covalently linking said agent to said polyglutamic acid polymer to form a polyglutamic acid-therapeutic agent conjugate;

(d) precipitating said polyglutamic acid-therapeutic agent conjugate from solution by the addition of an excess volume of aqueous salt solution; and (e) collecting said conjugate as a protonated solid.

The in situ procedure eliminates multiple steps in preparing the protonated PG polymer and reduces the overall process time by up to a week. In addition, the product appears to dissolve in aqueous solutions more rapidly when produced by the in situ procedure in comparison with the other methods disclosed herein.

In this procedure, any anhydrous acid may be used in step (b) above provided that the salt of the conjugate base is soluble in the organic solvent selected for use in the procedure. Examples of suitable acids include trifluoroacetic acid, chloroacetic acid, bromobenzoic acid, chlorobenzoic acid, chlorophenoxyacetic acid, chlorophenylacetic acid, cyanoacetic acid, cyanobutyric acid, cyanophenoxyacetic acid, cyanopropionic acid, dichloroacetic acid, acetoacetic-acid, fumaric acid, hippuric acid, iodoacetic acid, lactic acid, malonic acid, mesaconic acid, naphthoic acid, nitrobenzoic acid, phthalic acid, methane sulfonic acid, HBr, HCl, and HI.

Steps (c), (d) and (e) are carried out as described above for the general procedures.

Table 1 shows a representative analysis for poly L-glutamic acid-paclitaxel conjugate prepared as described in Example 3 below. Table 2 shows a representative analysis for poly L-glutamic acid-paclitaxel conjugate prepared in situ as described in Example 7 below.

TABLE 1

| | | Analytical data | | | | | | |
|---|---|---|---|---|---|---|---|---|
| mass %[a] | total output [b](g) | % loading (UV)[c] | % loading (NMR)[d] | % free paclitaxel[e] | % residual MeCN[f] | % residual DMF[g] | % DIPU[h] | ROI[i] |
| 93.6 | 87.80 | 42.0 | 34.0 | 0.128 | 0.15 | 0.27 | 0.160 | 0.87 |

[a]% yield;
[b]grams of conjugate;
[c]grams paclitaxel/grams conjugate determined by UV method;
[d]grams paclitaxel/grams conjugate determined by NMR method;
[e]wt % free paclitaxel relative to conjugate;
[f]wt % residual acetonitrile relative to conjugate;
[g]wt % residual dimethylformamide relative to conjugate;
[h]diisopropylurea relative to conjugate;
[i]wt % residue on ignition.

TABLE 2

| | | Analytical data | | | |
|---|---|---|---|---|---|
| mass %[a] | total output[b] (g) | % loading (NMR)[d] | % residual MeCN[f] | % residual DMF[g] | % DIPU[h] |
| 95.1 | 0.485 | 36.0 | 0-0.01 | 0.01-0.45 | 0 |

[a]% yield;
[b]grams of conjugate;
[d]grams paclitaxel/grams conjugate determined by NMR method;
[f]wt % residual acetonitrile relative to conjugate;
[g]wt % residual dimethylformamide relative to conjugate;
[h]wt % diisopropylurea relative to conjugate.

The invention is illustrated by the following examples which should not be regarded as limiting the scope of the invention in any way.

EXAMPLES

In the following examples, the intermediates in the production of the conjugates were characterized by $^1$H NMR. The molecular weights of the polyglutamic acid (Na salt) used to prepare the conjugates exemplified below range from 20 kd to 50 kd, as specified by the supplier (Sigma Chemical Co., Milwaukee, Wis.) based on viscosity measurements. The average loading density of the conjugates was 37%

Example 1

Preparation of poly-L-glutamic Acid

Poly-L-glutamic acid sodium salt (85.9 g) (Sigma Chemical Co., 37kd MW determined by viscosity measurement) was dissolved in USP purified water (534 mL; 6.2 mL/g), and the solution was cooled to between 0° C.-5° C. Dilute hydrochloric acid solution (1M) was added dropwise with vigorous stirring keeping the temperature <10° C. until the pH was between pH 2 to 2.5. During the addition, the poly-L-glutamic acid separated out of solution. The reaction mixture was warmed to room temperature and stirred for 1 hour. The suspension was centrifuged at 2700×g for 10 minutes. The upper aqueous layer was removed and the solid was resuspended in 560 mL USP purified water and recentrifuged for 10 minutes. The upper aqueous layer was removed and the pH was measured. Washing was continued, if necessary, until the pH of the aqueous layer was >3.0. The wet solid was lyophilized on a LABCONCO™ freeze dry system until a constant weight was obtained. The wt % sodium was no greater than 7000 ppm as determined by ICP.

Example 2

Preparation of poly-L-glutamic acid-2'-paclitaxel Conjugate

Poly-L-glutamic acid (16.82 g), prepared as described in Example 1 above, was suspended in anhydrous N,N-dimethylformamide (180 mL), paclitaxel (9.923 g, 11.6 mmol) and N,N-dimethylaminopyridine (283 mg, 2.32 mmol). The reaction mixture was stirred for 30 minutes. A solution of N,N-diisopropylcarbodiiumide (1.903 g, 15.08 mmol) in N,N-dimethylformamide (50 mL) was added over a period of 3 hours using a syringe pump. After the addition, the reaction was stirred until complete (about 4 hours at room temperature). The reaction was cooled to 5° C.-10° C. and 10% sodium chloride solution (345 mL) was added slowly to precipitate out the poly-L-glutamic acid-paclitaxel conjugate. The precipitate was separated by transferring the mixture to a centrifuge flask and centrifuging it at 1500 g. The wet solid was resuspended in water (150 mL) and 1 M sodium bicarbonate solution (120 mL) was added slowly with vigorous stirring to bring the pH of the solution to pH 7. The reaction was stirred for an hour and filtered through a 0.2 micron filter to remove impurities. The filtrate was cooled to 0° C.-5° C. and HCl (1N) was added slowly with vigorous stirring until the pH of the solution was brought to pH 3. Stirring was continued for 30 minutes. The precipitated solid was centrifuged at 1500 g, and the wet solid was washed twice by suspending in water (150 mL) and centrifuging. The product was lyophilized to yield 24 g of poly-L-glutamic acid-paclitaxel conjugate (90% yield).

In the above procedure, the filtration step can be omitted by washing the solution with ethyl acetate (250 mL, 2×) to remove impurities.

Figure 3:
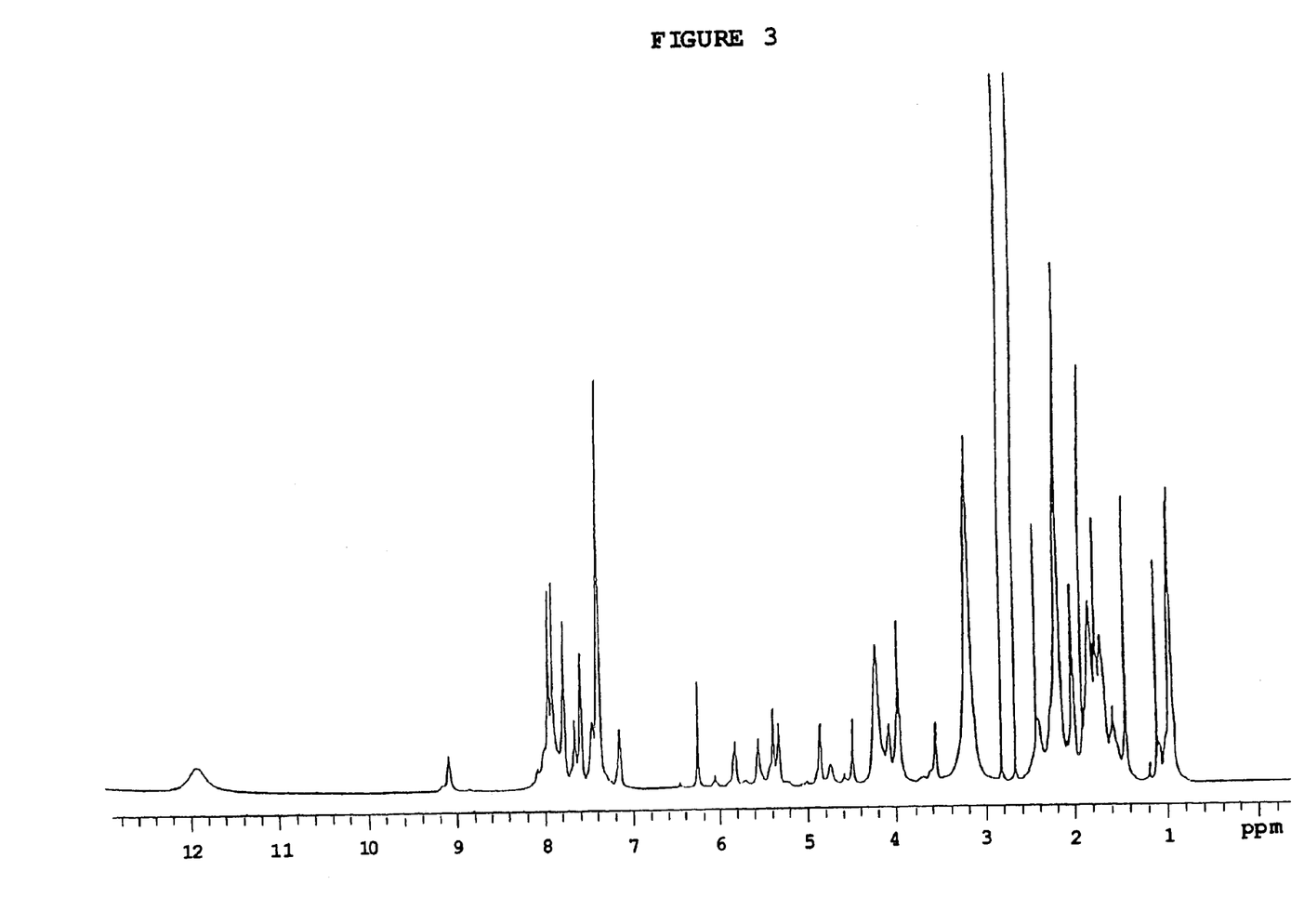
FIG. 3. Proton NMR scan of poly-L-glutamic acid paclitaxel conjugate

FIG. 3 shows a representative proton NMR scan for poly-L-glutamic acid-2'-paclitaxel conjugate prepared by same procedure as described above, but having a higher paclitaxel loading (i.e., 55%).

Example 3

Preparation of poly-L-glutamic acid-2'-paclitaxel Conjugate (Manufacturing Process)

Poly-L-glutamic acid (42 g), prepared as described in Example 1 above, was added to a three-necked three liter round bottom flask equipped with a mechanical stirrer, addition funnel and a thermo probe. N,N-dimethylformamide (350 mL) was added and stirred for 10 minutes. Paclitaxel (24.66 g) and N,N-dimethylaminopyridine (0.70 g) was added and stirred for 10 minutes. A solution of N,N-diisopropylcarbodiimide (4.73 g) in N,N-dimethylformamide (143 mL) was added at room temperature over a period of 1 hr using the addition funnel and was stirred for four hours. The reaction mixture was cooled to 5° C.-10° C. and a cooled solution of 10% sodium chloride (1.2 L) was added dropwise using an addition funnel and keeping the temperature at 5° C.-10° C. by cooling the flask in an ice-salt mixture. After the addition of sodium chloride solution, 1N solution of hydrochloric acid (35 mL) was added dropwise until the pH of the reaction reached 2.5. The reaction mixture was stirred for 30 minutes at 5° C.-10° C. and the precipitated poly-L-glutamic acid-paclitaxel conjugate was collected by filtration. The solids were washed three times with water and freeze dried in a lyophilizer for 24 hours. The dried solid was powdered into a fine powder using a mortar and pestle. The finely powdered poly-L-glutamic acid-paclitaxel conjugate was suspended in acetonitrile (1000 mL) and stirred for 2 hrs, then filtered and the solid was washed with 2×200 mL of acetonitrile. The solid was dried under vacuum for 24 hrs to give poly-L-glutamic acid-paclitaxel conjugate (60 g). Yield (90%).

Example 4

Preparation of poly-L-glutamic acid-glycine-paclitaxel Conjugate (Reaction Scheme II)

Steps 1 and 2 below were carried out essentially as described in Mathew et al. (Mathew, A. E., Mejillano, M. R., Nath, J. P., Himes, R. H., and Stella, V. J., *J. Med. Chem.*, 35:145-151, 1992).

Step 1. Preparation of 2'-(N-t-BOC-glycyl)paclitaxel

To a solution of N-t-BOC-L-glycine (131 mg, 0.75 mmol) and paclitaxel (640 mg, 0.75 mmol) in dichloromethane (20 mL) was added 1,3-diisopropylcarbodiimide (124 mg, 0.98 mmol) followed by N,N-dimethylaminopyridine (27 mg, 0.23 mmol). After stirring at room temperature for 4 hours, the mixture was concentrated under reduced pressure. The residue was purified by silica gel flash chromatography eluting with 1:1 (v/v) ethyl acetate/hexane to yield 2'-(N-t-BOC-glycyl)paclitaxel (720 mg, 95% yield) as a white powder.

Step 2. Preparation of 2'-(glycyl)paclitaxel

A solution of 2'-(N-t-BOC-glycyl)paclitaxel (245 mg, 0.242 mmol) in formic acid (2 mL) was stirred for 30 minutes. After concentrating under reduced pressure, the residue was suspended in water (15 mL). Cold 0.05 M sodium bicarbonate solution (45 mL) was added and the solution (pH 8.0) was extracted with dichloromethane (2×40 mL). The combined dichloromethane extracts were dried over anhydrous sodium sulfate and concentrated under reduced pressure. The residue was purified by silica gel flash chromatography eluting with 4% methanol/dichloromethane to yield 2'-(glycyl)paclitaxel (161 mg, 73% yield) as a white powder.

Step 3. Preparation of poly-L-glutamic acid-2'-(glycyl) paclitaxel Conjugate

To a stirred suspension of poly-L-glutamic acid (275 mg, 1.87 mmol) in anhydrous dimethylformamide (6 mL) was added 2'-(glycyl)paclitaxel (161 mg, 0.177 mmol). A solution of 1,3-diisopropylcarbodimide (29 mg, 0.23 mmol) in dimethylformamide (1.4 mL) was added to the stirred suspension over a period of 30 minutes. After stirring at room temperature for 3 hours, the mixture was cooled in an ice bath to bring the bath temperature to 0° C.-5° C. and then 10% aqueous sodium chloride solution (7 mL) was added over a period of 30 minutes to precipitate the poly-L-glutamic acid-2'-(glycyl)

paclitaxel conjugate. The resulting white suspension was centrifuged at 1500 g, 15 minutes. After filtration, the solid was washed twice by suspension in water (10 mL) and centrifugation. The crude product was suspended in water (6 mL) and a 1 M aqueous sodium bicarbonate solution (2.3 mL) was added slowly with stirring to bring the contents of the flask to pH 7.6. After stirring for an additional 2 hours, the aqueous layer was washed with ethyl acetate (3×6 mL) and then acidified by addition of 1N hydrochloric acid to pH 2.8. The precipitated solid was separated by centrifugation and washed with water (2×6 mL). The wet solid was lyophilized to give poly-L-glutamic acid-2'-(glycyl)paclitaxel conjugate (315 mg, 72% yield) as a white powder.

Using a similar procedure, the above conjugate can be substituted by amino acids other than glycine.

Example 5

Preparation of poly-L-glutamic acid-2'-docetaxel Conjugate (Reaction Scheme III)

Step 1. Preparation of 10-deacetylpaclitaxel

10-Deacetylpaclitaxel was prepared essentially as described in Zheng, Q. Y., Darbie, L. G., Chen, X., Murray, C. K., *Tetrahedron Letters.*, 36:2001-2004, 1995 and U.S. Pat. No. 5,629,433.

To a solution of paclitaxel (1.0 g, 1.17 mmol) in tetrahydrofuran (20 mL) was added hydrogen peroxide (30%, 20 mL) followed by sodium bicarbonate (1.92 g, 22.85 mmol). After stirring at room temperature for 18 hrs, the mixture was treated with dichloromethane/water (1:1(v/v), 100 mL). The organic phase was washed with water (2×30 mL), dried over anhydrous magnesium sulfate, and concentrated under vacuum. The residue was purified by silica gel flash chromatography eluting with 3% methanol/dichloromethane (v/v) to yield 10-deacetylpaclitaxel (890 mg, 93% yield) as a white powder.

Step 2. Preparation of 2',7-bis(triethylsilyl)-10-deacetylpaclitaxel 2',7-Bis(triethylsilyl)-10-deacetylpaclitaxel was prepared as described in U.S. Pat. No. 5, 629,433.

To a solution of 10-deacetylpaclitaxel (850 mg, 1.05 mmol) in anhydrous pyridine (20 mL was added chlorotriethysilane (2.72 mL, 20.1 mmol)at room temperature over a period of 30 minutes under an argon atmosphere. After stirring for 17 hours, the mixture was treated with dichloromethane (75 mL), washed with water (3×30 mL), with 10% aqueous copper sulfate solution (4×35 mL), with water (30 mL), and with saturated aqueous sodium chloride solution (30 mL): The organic layer was dried over anhydrous magnesium sulfate and concentrated under reduced pressure to provide 2',7-bis(triethylsilyl)-10-deacetylpaclitaxel (980 mg, 90% yield) as a powder.

Step 3. Preparation of 2',7-bis(triethylsilyl)-10-deacetylpaclitaxel Imine

2',7-Bis(triethylsilyl)-10-deacetylpaclitaxelimine was prepared as described in U.S. Pat. No. 5,629,433.

To a solution of 2',7-bis(triethylsilyl)-10-deacetylpaclitaxel (730 mg, 0.70 mmol) in tetrahydrofuran (7.3 mL) was added zirconocene chloride hydride (543 mg, 2.11 mmol). After stirring at room temperature under an agron atmosphere for 15 hours, the mixture was poured into cold hexanes (75 mL). The precipitated zirconium complexes were removed by filtration. The filtrate was concentrated under reduced pressure to give 2',7-bis(triethylsilyl)-10-deacetylpaclitaxelimine (636 mg, 92% yield) as a white powder.

Step 4. Preparation of 10-deacetylpaclitaxel Primary Amine

10-Deacetylpaclitaxel primary amine was prepared according to U.S. Pat. No. 5,629,433.

A solution of 2',7-bis(triethylsilyl)-10-deacetylpaclitaxel imine (636 mg, 0.621 mmol) in 1% (w/w) conc hydrochloric acid/95% ethanol (25 mL) was stirred for 15 hours, treated with water (65 mL), and washed with hexanes (2×30 mL). The aqueous layer was neutralized (pH 7) by addition of saturated aqueous sodium bicarbonate solution and extracted with dichloromethane (2×40 mL). The combined extracts were dried over anhydrous magnesium sulfate and concentrated under reduced pressure to yield the crude primary amine product (405 mg, 92% yield) as a white powder. This product was used for the next step without further purification.

Step 5. Preparation of Docetaxel

Docetaxel was prepared according to U.S. Pat. No. 5,629, 433.

To a solution of 10-deacetylpaclitaxel primary amine (405 mg, 0.57 mmol) in ethyl acetate (40 mL) was added saturated aqueous sodium bicarbonate solution (40 mL). To this biphasic mixture was added di-tert-butyldicarbonate (225 mg, 1.03 mmol). After stirring at room temperature for 15 hours, ethyl acetate (75 mL) was added. The organic phase was washed with water (2×30 mL), dried over anhydrous sodium sulfate, and concentrated under vacuum. The residue was purified by silica gel flash chromatography eluting with 4% methanol/dichloromethane to provide docetaxel (351 mg, 76% yield) as a white powder.

Step 6. Preparation of poly-L-glutamic acid-2'-docetaxel Conjugate

To a suspension of poly-L-glutamic acid (658 mg, 4.47 mmol) in anhydrous dimethylformamide (10 mL) was added docetaxel (385 mg, 0.48 mmol) and N,N-dimethylaminopyridine (12 mg, 0.096 mmol). To this stirred suspension was added a solution of 1,3-diisopropylcarbodiimide (78.8 mg, 0.624 mmol) dimethylformamide (3 mL) dropwise over 20 minutes. After stirring for 15 hours, the mixture was cooled in an ice bath and 10% aqueous sodium chloride solution (20 mL) was added over 30 minutes. After stirring for an additional 1 hour, the solid was filtered and the filtered cake was washed with water (4×50 mL). The solid was lyophilized to constant weight and then triturated with acetonitrile (4×50 mL). Drying under high vacuum for 15 hours provided poly-L-glutamic acid-2'-docetaxel conjugate (890 mg, 87% yield) as a white powder. $^1$H NMR (300 MHz, DMSO-$d_6$): δ 12.10 (s, —COO$\underline{H}$), 7.05-8.20 (m, aromatic protons), 4.80-6.05 (m), 3.80-4.50 (m), 5.0-5.6 (m, 5-$\underline{H2}$, 7-$\underline{H2}$), 3.70-4.35 (m), 1.20-2.80 (m), 1.00(s).

Example 6

Preparation of poly-l-glutamic acid-glycyl-20(S)camptothecin (Reaction Scheme I)

Steps 1 and 2 below were carried out as described by Greenwald, R. B., Pendri, A., Conover, C. D., Lee, C., Choe, Y. H., Gilbert, C., Martinez, A., Xia, J., Wu, D., and Hsue, M., *Bioorg. & Med. Chem.*, 6:551-562, 1998.

Step 1. Preparation of 20-(N-t-BOC-glycyl)-20(S)camptothecin

To a solution of N-t-BOC-glycine (530 mg, 3.0 mmol) in anhydrous dichloromethane (240 mL) was added 1,3-diisopropylcarbodiimide (379 mg, 3.0 mmol), N,N-dimethylaminopyridine (244 mg, 2 mmol), and 20(S)camptothecin (348 mg, 1.0 mmol) at 0° C. The reaction mixture was allowed to warm to room temperature. After stirring for 18 hours, the mixture was washed sequentially with 0.1N aqueous hydrochloric acid solution (2×50 mL), with water (2×50 mL), with 0.1 M aqueous sodium bicarbonate solution (2×25 mL), and with water (2×50 mL). The organic phase was dried over anhydrous sodium sulfate and concentrated under reduced pressure. The residue was crystallized from methanol (7 mL) to provide 20-(N-t-BOC-glycyl)-20(S)camptothecin (424 mg, 84% yield) as a yellow powder. $^1$H NMR (300 MHz, CDCl$_3$): δ 8.35 (s, 1H), 8.22 (d, J=8.38 Hz 1H), 7.91(d, J=8.07, 1H), 7.76-7.85 (m, 1H), 7.65 (t, J=7.4 Hz, 1H), 7.26 (s, 1H), 5.70 (d, J=17.25 Hz, 1H), 5.40 (d, J=17.25 Hz, 1H), 5.25 (s, 2H), 4.95 (br s, 1H), 3.98-4.25 (m, 2H), 2.18-2.26 (m, 2H), 1.38 (s, 9H), 0.95 (t, J=7.47 Hz, 3H).

Step 2. Preparation of 20-Glycyl-20(S)camptothecin Trifluoroacetic Acid Salt

A solution of 20-(N-t-BOC-glycyl)-20(S)camptothecin (424 mg, 0.84 mmol) in a 1:1 (v/v) mixture of dichloromethane/trifluoroacetic acid (21 mL) was stirred at room temperature for 1 hour. The solvents were evaporated under reduced pressure. The yellow solid was crystallized from dichloromethane/diethyl ether (3:7 (v/v), 50 mL) to provide 20-glycyl-20(S)camptothecin trifluoroacetic acid salt (361 mg, 83% yield) as a light yellow powder. $^1$H NMR (300 MHz, DMSO-d$_6$): δ 8.78 (s, 1H), 8.45 (br s, 2H), 8.20 (d, J=8.2 Hz 1H), 7.70-7.95 (m, 2H), 7.30 (s, 1H), 5.55 (s, 2H), 5.30 (s, 2H), 4.35 (d, J=17.9 Hz, 1H), 4.15 (d, J 17.9 Hz, 1H), 2.10-2.30 (m, 2H), 1.00 (t, J=7.4 Hz, 3H).

Step 3. Preparation of poly-L-glutamic acid-20-glycyl-20(S) camptothecin Conjugate To a stirred suspension of 20-glycyl-20(S)camptothecin trifluoroacetic acid salt (351 mg, 0.68 mmol), poly-L-glutamic acid (465 mg, 3.16 mmol), and N,N-dimethylaminopyridine (249 mg, 2.04 mmol) in anhydrous dimethylformamide (13 mL) was added a solution of 1,3-diisopropylcarbodiimide (111.6 mg, 0.88 mmol) in dimethylformamide (2 mL) over 20 minutes. After stirring under an argon atmosphere for 2 days, the mixture was cooled in an ice bath and 10% aqueous sodium chloride solution (35 mL) was added over 30 minutes. After stirring for an additional 1 hour, the suspension was acidified to pH 2.5 by addition of 1 N aqueous hydrochloric acid solution. The yellow precipitate was collected by filtration, washed with water (5×25 mL), dried under vacuum overnight, and triturated with acetonitrile (100 mL). After drying under high vacuum for 24 hours, poly-l-glutamic acid-20-glycyl-20(S)camptothecin conjugate (703 mg, 95% yield) was obtained as a yellow powder. $^1$H NMR (300 MHz, DMSO-d$_6$): δ12.10 (s, —COOH),7.05-8.74 (m, 7, 9, 10, 11, 12, & 14 CH), 5.0-5.6 (m, 5-CH2, 7-CH2), 3.70-4.3 5 (m, -Gly-CH2, PG-N-CH-), 1.42-2.62 (m, 18-CH2, PG-δCH2, δCH2), 0.90 (br s, 19-CH3). $^1$H NMR indicated a 20(S)camptothecin loading of 34%.

Example 7

In Situ Method for Generating Polyglutamic acid-Paclitaxel

A 100 mL round bottomed flask was charged with a stirbar, poly-(L-glutamic acid, sodium salt) (340 mg, 2.25 mmol, 11.3 eq), and 7 mL of dry dimethylformamide. The suspension was stirred and trifluoroacetic acid (156 μL, 2.03 mmol, 10.2 eq) was added neat via syringe. The suspended solid dissolved in ca. 5 minutes. Paclitaxel (170 mg, 0.199 mol, 1.0 eq) was added as a solid, followed by 4-(N,N-dimethylamino) pyridine (10 mg, 0.082 mmol, 0.4 eq) and diisopropylcarbodiimide (40 μL, 0.259 mmol, 1.3 eq). The solution was stirred at room temperature for 18 hours and was then cooled to 0° C. with an ice bath. A solution of 10 wt % aqueous sodium chloride was added slowly with vigorous stirring, resulting in precipitation of a fine white solid. The pH was adjusted to 2.5 with dilute hydrochloric acid and the suspension transferred to a 50 mL centrifuge tube. The solid was spun, the supernatant was decanted, and the resulting material was suspended in 35 mL of water. The suspension was again spun, decanted, and resuspended in 35 mL water. After this final rinse, the remaining material was lyophilized to obtain a dry powder. The powder was rinsed with 3×15 mL of acetonitrile and then the remaining solvent was removed under high vacuum, affording 485 mg of a white powder. $^1$H NMR (d$_6$ DMSO) indicated a paclitaxel loading of 38% by weight.

Example 8

Biological Assay

Antitumor activity was assayed in mice implanted subcutaneously with Lewis lung carcinoma cells (LL/2). Tumors were produced in the muscle of the right interscapular region by subcutaneously injecting 2.5×10$^5$ murine Lewis Lung (LL/2) carcinoma cells (ATTC CRL-1642) in a volume of 0.25 ml PBS+2% FBS. Test compounds and vehicle control were injected ip 7 days after tumor cell implantation when the tumors had grown to 20±20 mm$^3$ (average of 230 tumors). A single dose of polyglutamic acid-therapeutic agent conjugate in 0.1N Na$_2$HP0$_4$ was administered at a 1×-4× the maximum tolerated equivalent dose of the unconjugated agent, which was typically administered in 8.3% cremophore EL/8.3% ethanol in 0.75% saline. Each treatment group consisted of 10 mice randomly allocated to each group. Initially, tumor growth was monitored every 3 to 4 days. When tumor sizes approached the arbitrarily set upper limit of 2500 mm$^3$, tumor sizes were determined daily. Tumor volume was calculated according to the formula (length×width×height)/2. Mice with tumors equal to or greater than 2500 mm$^3$ were euthanized by cervical dislocation. Efficacy of the various treatments was expressed in terms of days for tumor to reach a volume of 2500 mm$^3$ (i.e., TGD, tumor growth delay) compared with maximum tolerated dose of the unconjugated therapeutic agent.

The PG-therapeutic agent conjugates described in Examples 2, 3, 5 and 6 above were tested and found to be active in this assay.

Example 9

Preparation of poly-L-glutamic acid-CT 2584

Poly-L-glutamic acid (4.95 g) was suspended in anhydrous N,N-dimethyl formamide (120 mL) and CT 2584 (0.873 g, 1.634 mmol) was added. The reaction mixture was warmed with stirring to 50° C. until a clear solution was formed. The reaction mixture was cooled back to room temperature and a solution of N,N-diisopropylcarbodiimide (0.247 g, 1.96 mmol) in N,N-dimethylformamide (5 mL) was added over a period of 30 minutes using a dropping funnel. After the addition, the reaction was stirred for 4 hrs at room temperature. The reaction was cooled to 5° C.-10° C. and 10% sodium chloride solution (200 mL) was added slowly to precipitate out the poly-L-glutamic acid CT 2584 conjugate. The precipitate was collected by centrifuging at 1500×g. The wet solid was washed twice by suspending in water (150 mL) and centrifuging. The product was freeze dried to give 5.16 grams of poly-L-glutamic acid CT 2584 conjugate. Yield=88.6%.

The product was characterized by $^1$H NMR, which showed a singlet at 3.9 ppm and 3.4 ppm corresponding to methyl group at N3 and N7 and a broad singlet at 1.24 ppm corresponding to the alkyl protons and a broad peak at 0.85 ppm for the terminal methyl group of CT 2584. In addition NMR showed multiplets between 1.5 ppm-3.0 ppm and 3.5 ppm-4.5 ppm corresponding to poly-L-glutamic acid backbone.

Example 10

Preparation of Poly-L-glutamic acid-camptothecin

A mixture of 20(S)-camptothecin (64 mg, 0.184 mmol), poly-(L-glutamic acid) (256 mg, 49.8 kD) was dried under vacuum for 6 hours, then dissolved in anhydrous dimethylformamide (15 mL). The solution was cooled to −5° C. in an ice/salt bath. To this was added under argon 2-chloromethylpyridinium iodide (85 mg, 0.33 mmol) and N,N-dimethylaminopyridine (81 mg, 0.66 mmol). The reaction mixture was allowed to warm to room temperature overnight. After 4 days, the reaction flask was again cooled to 0° C. and 10% sodium chloride solution (35 mL) was slowly added during 25 minutes. This mixture was acidified to pH 2.5 using 0.5N HCl (3.5 mL) and then stirred at room temperature for an additional hour. The yellow precipitate which formed was filtered, washed with water (4×30 mL), then dried under vacuum for 12 hours. The dry yellow cake obtained was ground to a fine powder, resuspended in 2% MeOH/CH$_2$Cl$_2$ (10 mL) and stirred for 3 hours. The solid was separated by centrifugation. This process was repeated four times to remove any unreacted camptothecin. The resulting solid was dried under vacuum for 2 days, to yield PG-20(S)-camptothecin (295 mg, 97% yield, determined by weight balance on the basis of the recovered camptothecin (13 mg)). $^1$H NMR (300 MHz in DMSO-d$_6$): δ 12.10 (s, —COO$\underline{H}$), 6.90-8.80 (m), 5.15-5.8 (m), 3.10-4.35 (m), 1.42-2.62 (m), 0.90 (br s, 19—C$\underline{H}_3$). The paclitaxel % loading was 16% by weight.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

All of the publications, patent applications and patents cited in this application are herein incorporated by reference in their entirety to the same extent as if each individual publication, patent application or patent was specifically and individually indicated to be incorporated by reference in its entirety.

What is claimed is:

1. A polyglutamic acid-camptothecin conjugate having the formula:

wherein:

PG is polyglutamic acid polymer; and camptothecin is selected from the group consisting of 20(S)-camptothecin, 20(S)-9-aminocamptothecin, 20(S)-9-nitrocamptothecin, 20(S)-7-ethyl-10-hydroxycamptothecin, 9-dimethylaminomethyl-10-hydroxycamptothecin, 10,11-methylenedioxycamptothecin, and 7-methylpiperizinomethyl-10,11-ethylenedioxycamptothecin.

2. The conjugate of claim 1, wherein the weight % ratio of said camptothecin to said PG is about 1-60%.

3. The conjugate of claim 1, wherein the weight % ratio of said camptothecin to said PG is 10-45%.

4. The conjugate of claim 1, wherein said camptothecin is selected from 20(S)-camptothecin, 20(S)-9-aminocamptothecin, 20(S)-9-nitrocamptothecin, and 20(S)-7-ethyl-10-hydroxycamptothecin.

5. The conjugate of claim 4, wherein said camptothecin is 20(S)-camptothecin.

6. The conjugate of claim 5, wherein the weight % ratio of said 20(S)-camptothecin to said PG is 34%.

7. A method of preparing a polyglutamic acid-camptothecin conjugate having the formula:

wherein:

PG is polyglutamic acid polymer; and camptothecin is selected from the group consisting of 20(S)-camptothecin, 20(S)-9-aminocamptothecin, 20(S)-9-nitrocamptothecin, 20(S)-7-ethyl-10-hydroxycamptothecin, 9-dimethylaminomethyl-10-hydroxycamptothecin, 10,11-methylenedioxycamptothecin, and 7-methylpiperizinomethyl-10,11-ethylenedioxycamptothecin wherein said method comprises:

(a) providing a polyglutamic acid polymer having a MW of about 20,000 to about 60,000 daltons, as determined by viscosity, and camptothecin for conjugation thereto;

(b) attaching a glycine linker to the camptothecin, wherein the glycine linker consists of a single glycine residue; and (c) covalently linking said camptothecin to said polyglutamic acid polymer via the glycine linker under conditions sufficient to attach at least 5 molecules of the camptothecin per chain of polymer, thereby forming said polyglutamic acid-camptothecin conjugate.

8. The method of claim 7, wherein the weight % ratio of said camptothecin to said PG is 1-60%.

9. The method of claim 7, wherein the weight % ratio of said camptothecin or analog thereof to said PG is 10-45%.

10. The method of claim 7, wherein the weight % ratio of said camptothecin to said PG is 34%.

11. A pharmaceutical composition comprising the polyglutamic acid-camptothecin conjugate of claim 1 or a pharmaceutically acceptable salt thereof and a pharmaceutically acceptable carrier and/or diluent.

12. The pharmaceutical composition of claim 11, wherein said camptothecin is 20(S)-camptothecin.

13. The pharmaceutical composition of claim 12, wherein the weight % ratio of said 20(S)-camptothecin to said PG is 1-60%.

14. The pharmaceutical composition of claim 12, wherein the weight % ratio of said 20(S)-camptothecin to said PG is 10-45%.

15. The pharmaceutical composition of claim 12, wherein the weight % ratio of said 20(S)-camptothecin to said PG is 34%.

16. A conjugate comprising a polyglutamic acid polymer covalently bonded to a camptothecin molecule selected from the group consisting of 20(S)(+)-camptothecin, 9-aminocamptothecin, 9-nitrocamptothecin, 7-ethyl-10-hydroxycamptothecin, 9-dimethylaminomethyl-10-hydroxycamptothecin and 7-methylpiperizinomethyl-10, 11-ethylenedioxy-camptothecin, wherein said polyglutamic acid is bonded to said camptothecin molecule by an indirect linkage consisting of one or more glycine residues.

17. The conjugate of claim 16, wherein said indirect linkage is via one glycine residue.

18. The conjugate of claim 16, wherein said camptothecin molecule is 20(S)(+)-camptothecin.

19. The conjugate of claim 18, wherein said conjugate is poly-1-glutamic acid-glycyl-20(S)(+)-camptothecin.

20. The conjugate of claim 16, wherein said conjugate comprises 1-60% by weight of said camptothecin.

21. The conjugate of claim 20, wherein said conjugate comprises 10-45% by weight of said camptothecin.

22. The conjugate of claim 21, wherein said conjugate is poly-L-glutamic acid-20-glycyl-20(S)camptothecin and wherein said conjugate comprises 34% by weight of said camptothecin molecule.

23. The conjugate of claim 16, wherein said polyglutamic acid polymer has a molecular weight from 20 kD to 60 kD as determined by viscosity.

24. A pharmaceutical composition comprising the conjugate of claim 16 or a pharmaceutically acceptable salt thereof and a pharmaceutically acceptable carrier and/or diluent.

25. A process for preparing a conjugate according to claim 16, comprising:
(a) providing the protonated form of a polyglutamic acid polymer and a camptothecin molecule selected from the group consisting of 20(S)(+)-camptothecin, 9-aminocamptothecin, 9-nitrocamptothecin, 7-ethyl-10-hydroxycamptothecin, 9-dimethyl-aminomethyl-10-hydroxycamptothecin and 7-methylpiperizinomethyl-10, 11-ethylenedioxy-camptothecin for conjugation thereto; and
(b) covalently linking said camptothecin molecule to said polyglutamic acid polymer via a linker in an inert organic solvent to form a polyglutamic acid-camptothecin conjugate, wherein said linker consists of one or more glycine residues.

* * * * *